(12) United States Patent
Solsberg

(10) Patent No.: US 7,799,247 B2
(45) Date of Patent: Sep. 21, 2010

(54) DISPOSABLE CHEMILUMINESCENT INFRARED THERAPY DEVICE

(76) Inventor: Murray David Solsberg, 15 Huntwick La., Englewood, CO (US) 80113

( * ) Notice: Subject to any disclaimer, the term of this patent is extended or adjusted under 35 U.S.C. 154(b) by 0 days.

(21) Appl. No.: 12/590,485

(22) Filed: Nov. 9, 2009

(65) Prior Publication Data

US 2010/0063567 A1    Mar. 11, 2010

Related U.S. Application Data

(60) Continuation of application No. 12/012,324, filed on Feb. 1, 2008, now Pat. No. 7,628,939, which is a division of application No. 10/969,253, filed on Oct. 19, 2004, now abandoned.

(60) Provisional application No. 60/514,196, filed on Oct. 24, 2003.

(51) Int. Cl.
*A61B 18/18* (2006.01)
*C09K 3/00* (2006.01)
*F21K 2/06* (2006.01)

(52) U.S. Cl. ............... 252/700; 362/34; 606/2; 606/17; 606/18; 607/88

(58) Field of Classification Search ............... 252/700; 362/34; 606/2, 17, 18; 607/88
See application file for complete search history.

(56) References Cited

U.S. PATENT DOCUMENTS

| | | | |
|---|---|---|---|
| 3,539,794 A | 11/1970 | McKay et al. |
| 4,379,320 A | 4/1983 | Mohan et al. |
| 4,678,608 A | 7/1987 | Dugliss |
| 4,717,511 A | 1/1988 | Koroscil |
| 4,751,616 A | 6/1988 | Smithey |
| 4,814,949 A | 3/1989 | Elliot |
| 4,838,457 A * | 6/1989 | Swahl et al. ............... 222/48 |
| 4,976,706 A | 12/1990 | Aki et al. |
| 5,067,051 A | 11/1991 | Ladyjensky |
| 5,121,302 A | 6/1992 | Bay et al. |
| 5,358,503 A | 10/1994 | Bertwell et al. |
| 5,430,622 A | 7/1995 | Kuo |
| RE35,007 E | 8/1995 | Cohen et al. |
| 5,488,544 A | 1/1996 | Ladyjensky |
| 5,552,968 A | 9/1996 | Ladyjensky |
| 5,705,103 A | 1/1998 | Chopdekar et al. |
| 5,766,233 A | 6/1998 | Thiberg |
| 5,800,479 A | 9/1998 | Thiberg |
| 5,842,786 A * | 12/1998 | Solomon ............... 366/139 |
| 6,026,330 A | 2/2000 | Chuang |
| 6,106,129 A | 8/2000 | Cranor et al. |
| 6,126,871 A | 10/2000 | Cranor |

(Continued)

OTHER PUBLICATIONS

Horowitz, et al, "Augmentation of Wound Healing Using Monochromatic Infrared Energy", in Advances in Woundcare, Jan./Feb. 1999.

(Continued)

*Primary Examiner*—Timothy J. Kugel
(74) *Attorney, Agent, or Firm*—Raymond Sun

(57) ABSTRACT

A therapeutic device has a first chamber that retains an oxalic ester solution, and a second chamber that retains a hydrogen peroxide and fluorescer solution. The therapeutic device is activated by causing the oxalic ester solution to mix with the hydrogen peroxide and fluorescer solution, which produces chemiluminescent light for treating a wound.

3 Claims, 2 Drawing Sheets

U.S. PATENT DOCUMENTS

| | | |
|---|---|---|
| 6,238,424 B1 | 5/2001 | Thiberg |
| 6,267,914 B1 | 7/2001 | Cranor |
| 6,461,543 B2 | 10/2002 | Earl |
| 6,471,716 B1 | 10/2002 | Pecukonis |
| 6,497,181 B1 | 12/2002 | Manole et al. |
| 6,510,346 B2 | 1/2003 | Gordon |
| 6,537,302 B1 | 3/2003 | Thiberg |
| 6,569,189 B1 | 5/2003 | Augustine et al. |
| 6,758,572 B2 | 7/2004 | Ladyjensky |
| 2002/0173780 A1 | 11/2002 | Altshuler et al. |
| 2003/0048631 A1 | 3/2003 | Ladyjensky |

OTHER PUBLICATIONS

Danno, et al., "Near-infrared irradiation stimulates cutaneous wound repair: laboratory experiments on possible mechanisms", Photodermatol Photoimmunol Photomed 2001: 17 261-265.

Chemiluminescence of oxalate esters, May 19, 2003.

\* cited by examiner

DISPOSABLE CHEMILUMINESCENT INFRARED THERAPY DEVICE

BACKGROUND OF THE INVENTION

1. Related Cases

Priority is claimed from Provisional Specification No. 60/514,196, filed Oct. 24, 2003. This is a continuation application of Ser. No. 12/012,324, filed Feb. 1, 2008, now U.S. Pat. No. 7,628,939, which is a division of Ser. No. 10/969,253, filed Oct. 19, 2004, now abandoned, whose disclosures are incorporated by this reference as though fully set forth herein.

2. Field of the Invention

The present invention relates to a self-contained disposable chemiluminescent device and method where chemical components react with a fluorescer to produce light in the infrared range for medical light therapy. The present invention also relates to devices used to separate the chemicals needed for the production of chemiluminescent light until the medical device is activated.

3. Description of the Related Art

Wound healing is a common and frequently challenging patient care issue, particularly when chronic ulcers occur. Factors that impair wound healing include diabetes, smoking, steroid therapy, poor nutrition, peripheral vascular disease and systemic infection. These processes reduce the available substrates and immune responses needed to heal a wound. In contrast, factors that enhance wound healing include strategies to increase local blood flow and oxygen content at the wound site.

Light therapy with infrared light is used to treat wounds and painful peripheral nerve disorders. It is hypothesized that infrared light stimulates the growth of new blood vessels (angiogenesis), thereby improving local blood flow and oxygen content. It is also hypothesized that infrared light increases nitrous oxide (NO) levels in tissues. Nitrous oxide is a potent vasodilator (i.e. relaxes the muscles in the wall of arteries) and therefore results in increased local blood flow. Infrared therapy has been shown to be effective in improving wound healing especially in patients suffering from pre-existing vascular disease. Infrared therapy has been shown to improve tensile strength of wounds and to improve flap survivability.

There are currently several commercially available infrared sources for medical light therapy. These devices use electric infrared sources such as light emitting diodes or laser technology, which require a source of electricity to power either the infrared emitting light emitting diodes or laser. Also, lasers and other infrared sources are more cumbersome to use and transport, and are more expensive.

Thus, there remains a need for improved infrared therapy which avoids the drawbacks associated with light emitting diodes and lasers.

SUMMARY OF THE INVENTION

It is an object of the present invention to provide a medical device for medical light therapy and bio-stimulation.

It is another object of the present invention to provide a disposable chemiluminescent infrared source and bandage for medical light therapy and bio-stimulation.

To accomplish these objectives, the present invention provides a therapeutic device having a first chamber that retains an oxalic ester solution, and a second chamber that retains a hydrogen peroxide solution. The therapeutic device is activated by causing the oxalic ester solution to mix with the hydrogen peroxide solution and a fluorescer, which produces chemiluminescent light for treating a wound.

DESCRIPTION OF THE PREFERRED EMBODIMENTS

Figure 1:
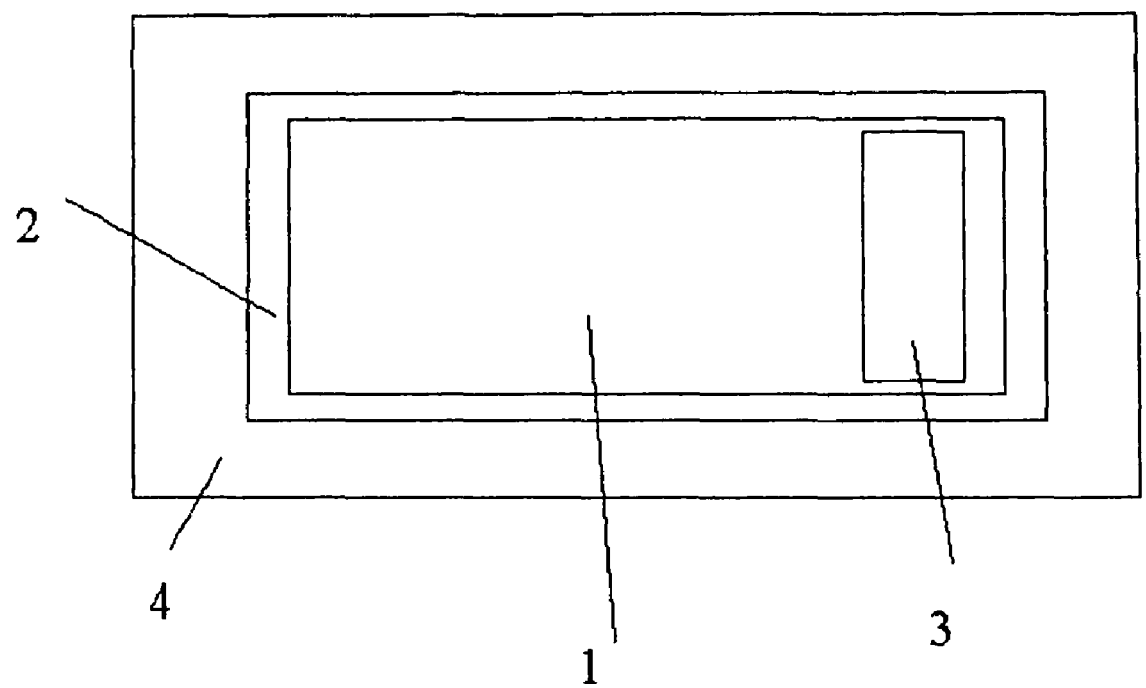
FIG. 1 is a top plan view of a chemiluminescent device according to one embodiment of the present invention.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention provides a disposable chemiluminescent infrared source and bandage for medical light therapy and bio-stimulation. Infrared light of a specific range of wavelengths in the 950 nm range is emitted when an oxalic ester is mixed with hydrogen peroxide and an infrared fluorescer molecule (and optionally, a catalyst) to this reaction. Known chemiluminescent non-toxic stable chemicals can be used. The specific wavelength emitted by chemiluminescence can be adjusted by the specific chemical composition appropriate to the specific application. Numerous different chemical compositions and fluorescers are available from the prior art to produce the specific wavelengths of light needed for medical light therapy. For example, see "Fluorescence and Phosphorescence" by Peter Pringsheim, Interscience Publishers, Inc., New York, N.Y., (1949), "The Colour Index," Third Edition, Volume 4, The Society of Dyers and Colourists, and The American Association of Textile Chemists and Colorists (1971). Others examples are described in "Dye Lasers" by F. P. Schaefer, Editor, Springer Publishers, Berlin (1973), and "Eastman Laser Products." Publication JJ-169, Eastman Kodak Company, Rochester, N.Y. (1977). These chemical compositions, as described above, are typically created by mixing an oxalic type ester and a peroxide (such as hydrogen peroxide), and use fluorescers such as fluoroscein, perylene dyes or derivatives, to produce light. U.S. Pat. Nos. 4,379,320, 4,678,608, 4,717,511, 5,122,306 and 5,232,635 illustrate other examples. Although the present invention illustrates the use of infrared wavelength range light for light therapy, it is also possible to use the principles of the present invention in other wavelengths for light therapy if desired.

The chemicals are stored in a two-compartment device to separate the chemicals until the chemiluminescent light is needed. The light generating device may have either a flexible or rigid configuration.

The flexible device can be composed of a thin inner 2 mil poly pouch that contains the dye solution. Approximately 10 ml of the oxalic ester solution mixed with a dilute indicator dye is placed in the thin inner poly pouch. The ends of this inner poly pouch are then heat sealed. The inner poly pouch is then placed within a thicker durable 6 mil poly tubing outer pouch and 40 cc of clear hydrogen peroxide is filled around the inner poly pouch. The ends of this outer poly pouch are then double heat sealed to prevent leakage. A thin aluminum foil reflective backing is placed on one side of outer poly pouch. This foil backing is an excellent reflector of infrared light, and bench tests indicate that this reflector increases the output of the device by over 50%.

The flexible device is activated by squeezing the inner pouch through the outer pouch. The inner poly pouch ruptures at about 2-4 pounds of force so even an elderly or infirm patient can activate it. The inner pouch also contains a colored but inert indicator dye. Infrared light is not visible to the human eye so that the indicator dye is useful to confirm activation of the device. The flexible device is stored in a rigid cardboard container prior to use to prevent accidental activation. The outer pouch can then be applied to the region that needs to be treated.

The rigid device can be composed of two plastic chambers. The upper and smaller chamber would contain the chemiluminescent fluorescer solution. The lower chamber would contain the hydrogen peroxide solution. There are a plurality of holes in the bottom of the upper chamber. The upper chamber screws into a snug, water tight round opening in the top of the lower chamber creating a seal and valve. A plurality of holes are positioned in the bottom of the upper chamber near to, but separate, from aligning holes in the lower chamber. The two chemicals are mixed by rotating the upper chamber until the holes in the upper and lower chambers are aligned to allow mixing of the chemicals. A first line on the outside of the upper chamber and a second line on the lower chamber are aligned when the holes are aligned, so as to show that the rigid device has been activated. The lower chamber can be lined on one side with a thin aluminum foil reflective backing beneath a vinyl backing containing the hydrogen peroxide solution. The bottom of the rigid device would be translucent.

A hypoallergenic adhesive plastic strip can be applied along the edge of the light emitting side of the flexible device and the rigid device. The sticky side is covered with a plastic strip until activated. After the device is activated, the patient then removes the plastic covering strips to expose the adhesive (like a BAND-AID) and applies the device to clean dry skin.

It was noticed that warming the solution to body temperature also approximately doubles the light output of the device. The duration of the chemical reaction production is approximately 2 hours.

Squeezing the inner pouch until it ruptures will activate the flexible device. Rotating the valve into the open position will activate the rigid device. The chemicals then mix and infrared light is released by the reaction. The pack can then be applied to a wound or painful limb. The devices can be manufactured in a variety of sizes as needed. The chemical reaction emits infrared light for approximately two hours at 37 degrees Celsius. The chemicals are non-toxic and therefore the device can be disposed of after use.

FIG. 1 illustrates an example of a flexible device according to the present invention. The flexible device has an outer pouch 1 that can be made of a durable vinyl or similar transparent material. The outer pouch 1 is covered on one side by a thin aluminum foil 2 that functions to reflect the produced infrared light onto the wound. As described above, hydrogen peroxide is filled inside the outer pouch 1. The inner pouch 3 is also retained inside the outer pouch 1, and contains the dye solution (e.g. oxalic ester solution and an indicator dye). The inner pouch 3 is made from a material that can be easily ruptured, such as a thin plastic. The edges of the inner pouch 3 are then heat sealed. An adhesive strip 4 is placed around the margin of the outer pouch 1 to hold the flexible device on the skin.

In use, the patient can press on the inner pouch 3 to rupture the inner pouch 3. The dye solution in the inner pouch 3 will mix with the hydrogen peroxide inside the outer pouch 1 to produce chemiluminescent infrared light that will be emitted towards the wound. The patient can then apply the adhesive strip 4 to the location of the wound.

Figure 2:
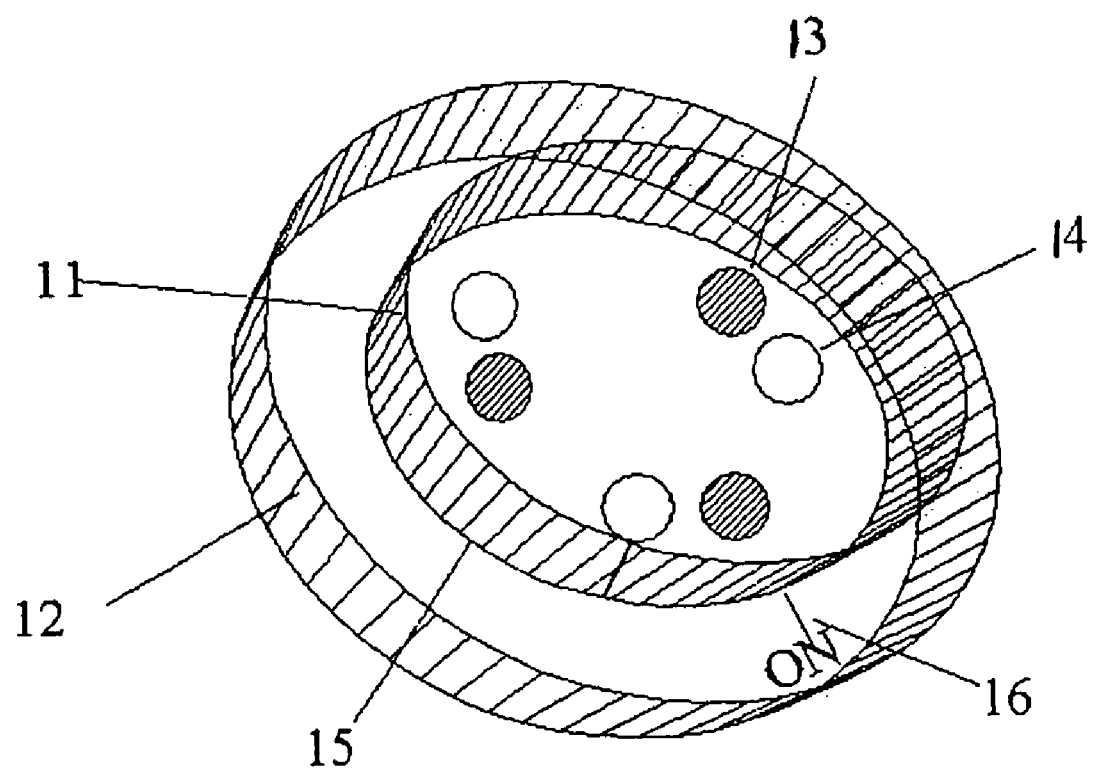
FIG. 2 is a perspective view of a chemiluminescent device according to another embodiment of the present invention.

FIG. 2 illustrates an example of a rigid device according to the present invention. The rigid device has an upper chamber 11 that contains the dye solution, and a lower chamber 12 that contains the hydrogen peroxide solution. The upper chamber 11 and the lower chamber 12 are both rigid chambers that can be made from a rigid material, such as plastic. The upper chamber 11 can have outer threads that are adopted to be screwed into a threaded opening 15 at the top of the lower chamber 12 to form a snug and water-tight seal and valve. A plurality of holes 13 are positioned at the bottom of the upper chamber 11 adjacent to but separate from the aligned holes 14 in the lower chamber 12. The chemicals from the respective chambers 11 and 12 are mixed by rotating the upper chamber 11 until the holes 13, 14 are aligned to allow the chemicals to mix. An indicator 16 is lined up when the holes 13, 14 are aligned. The rigid device can then be applied to the location of the wound. An adhesive strip (not shown), similar to adhesive strip 4, can be used to maintain the rigid device at the location of the wound.

While the description above refers to particular embodiments of the present invention, it will be understood that many modifications may be made without departing from the spirit thereof.

What is claimed is:

1. A therapeutic device, comprising:
    a first rigid chamber that retains an oxalic ester solution, the first chamber having a plurality of holes;
    a second rigid chamber that retains a hydrogen peroxide and fluorescer solution, the second chamber having a plurality of holes, and an opening that rotatably receives the first chamber; and
    wherein the holes of the first and second chambers are aligned by rotating the first chamber with respect to the second chamber so that the solution in the first chamber mixes with the hydrogen peroxide and fluorescer solution in the second chamber.

2. The device of claim 1, wherein the first chamber also contains a dye.

3. The device of claim 1, further including means for indicating that the holes of the first and second chamber are aligned.

* * * * *